United States Patent [19]

Willer

[11] 4,443,602

[45] Apr. 17, 1984

[54] TRANS-1,4,5,8-TETRANITRO-1,4,5,8-TETRAAZADECALIN

[75] Inventor: Rodney L. Willer, Ridgecrest, Calif.

[73] Assignee: The United States of America as represented by the Secretary of the Navy, Washington, D.C.

[21] Appl. No.: 349,134

[22] Filed: Feb. 16, 1982

[51] Int. Cl.$^3$ .......................................... C07D 487/22
[52] U.S. Cl. .................................................. 544/350
[58] Field of Search ................................. 544/350, 215

[56] References Cited

U.S. PATENT DOCUMENTS

| 1,402,693 | 1/1922 | von Herz | 544/215 |
| 2,345,236 | 3/1944 | Chitwood | 544/350 |
| 2,345,237 | 3/1944 | Chitwood et al. | 544/350 |
| 2,859,215 | 11/1958 | Spomer | 544/215 |

FOREIGN PATENT DOCUMENTS

| 454475 | 2/1949 | Canada | 544/350 |

*Primary Examiner*—Donald G. Daus
*Assistant Examiner*—James H. Turnipseed
*Attorney, Agent, or Firm*—Robert F. Beers; W. Thom Skeer; Bruce H. Cottrell

[57] ABSTRACT

The chemical compound, trans-1,4,5,8-tetranitro-1,4,5,8-tetraazadecalin (TNAD), is produced by the reaction of trans-1,4,5,8-tetraazadecalin with sodium nitrite and hydrochloric acid to obtain trans-1,4,5,8-tetranitroso-1,4,5,8-tetraazadecalin, followed by nitration to yield TNAD, useful as an explosive.

1 Claim, No Drawings

TRANS-1,4,5,8-TETRANITRO-1,4,5,8-TETRAAZADECALIN

BACKGROUND OF THE INVENTION

This invention relates to synthesis of a new propellant and explosive compound, trans-1,4,5,8-tetranitro-1,4,5,8-tetraazadecalin, (TNAD).

The compound has several physical properties which are superior to those of HMX (1,3,5,7-tetranitro-1,3,5,7-tetraazacyclooctane) and RDX (1,3,5-trinitro-1,3,5-hexahydrotriazine). These superior physical properties include heat stability and insensitivity to impact.

SUMMARY OF THE INVENTION

Trans-1,4,5,8-tetraazadecalin is reacted with sodium nitrite and hydrochloric acid, to obtain trans-1,4,5,8-tetranitroso-1,4,5,8-tetraazadecalin and the compound thus obtained is reacted with nitric acid at −30° C. to form 8-nitrose-1,4,5-trinitro-1,4,5,8-tetraazadecalin, which then is further reacted with additional nitric acid at 0° C. to give TNAD.

DESCRIPTION OF THE PREFERRED EMBODIMENT

TNAD is synthesized by first condensing ethylene diamine with glyoxal to obtain trans-1,4,5,8-tetraazadecalin, which is then converted into its tetranitroso derivative which is further nitrolysed.

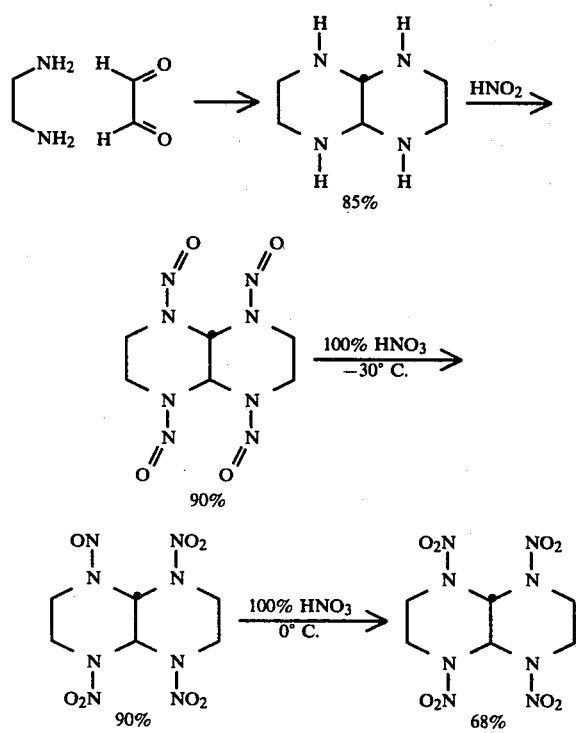

The examples below are intended to illustrate preferred embodiments of synthesizing the compounds of this invention.

EXAMPLE 1

Preparation of 1,4,5,8-Tetraazadecalin

In a 250-ml round bottom flask was placed 24.0 g of ethylene diamine (0.40 mole). This was cooled to 0° C. by a salt/ice bath and 14.5 g of 40% aqueous glyoxal solution (0.10 mole) was added dropwise during the next 30 minutes. This solution was then heated at 80° C. for 5 hours. During the heating period of crystals formed in the solution. The solution was allowed to slowly cool to room temperature, then cooled to 0° C. The product was then collected by vacuum filtration and washed with cold 50% ethanol. The yield of product m.p. 162°-170° C. (decomposition) is 12.0 g (0.085 mole, 85%).

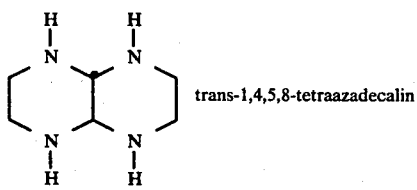

trans-1,4,5,8-tetraazadecalin

EXAMPLE 2

Preparation of 1,4,5,8-Tetranitroso-1,4,5,8-tetraazadecalin

A solution of 3.45 g (50 mmoles) sodium nitrite and 1.42 g (10 mmoles) of 1,4,5,8-tetraazadecalin was prepared in a 125-ml erlenmeyer flask. The temperature was not allowed to exceed 5° C. It was cooled to −2° C. and 50 ml of 1 N hydrochloric acid was added during the next 60 seconds. A white precipitate formed immediately. The mixture was stirred at 0° C. for 30 minutes, then at room temperature for 1 hour. The product was collected by vacuum filtration and washed well with water. It was dried overnight in a vacuum oven to give an off-white powder, which was suitable for further synthetic uses. It weighed 2.35 g (9.1 mmoles, 91%) and decomposed at 211°-212° C. It could be recrystallized from DMF/H$_2$O to yield fine light-yellow needles.

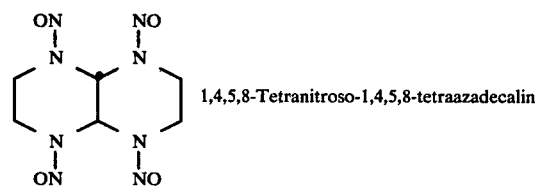

1,4,5,8-Tetranitroso-1,4,5,8-tetraazadecalin

EXAMPLE 3

8-Nitroso-1,4,5-trinitro-1,4,5,8-tetraazadecalin

Ten ml 100% nitric acid and a magnetic stirring bar were placed in a 50-ml erlenmeyer flask. This was cooled to −30° C. by a dichloroethane/dry ice slush. The 1,4,5,8-tetranitroso-1,4,5,8-tetraazadecalin (1.00 g, 3.87 mmoles) was added over 30 minutes. The dichloroethane/dry ice bath was removed and replaced by an ice bath. The mixture was stirred for an additional hour, then poured onto 50 g of ice. A fine white precipitate formed. The crude product was collected and washed well with water. After drying in vacuum, it weighed 1.07 g (3.52 mmoles, 90%) and decomposed at 210°-212° C. This compound contained small amounts of the tetranitro compound as evidenced by a small singlet in the NMR at 6.50 ppm.

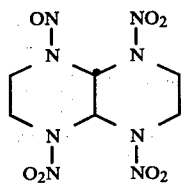

8-Nitroso-1,4,5-trinitro-1,4,5,8-tetraazadecalin

EXAMPLE 4

Preparation of 1,4,5,8-Tetranitro-1,4,5,8-tetraazadecalin

A portion of 8-nitroso-1,4,5-trinitro-1,4,5,8-tetraazadecalin (1.0 g, 3.3 mmoles) was slowly added to 10 ml of well-stirred 100% nitric acid maintained at 0° C. over a 15-minute time period. The solution developed a light-yellow color. It was stirred for 5 additional minutes at 0° C., then the coupling bath was removed. The stirring was continued for 5 more minutes. The reaction mixture was quenched by pouring onto 20 g of ice. A white precipitate formed and was collected by vacuum filtration. It was washed well with water and dried. It weighed 0.72 g (2.2 mmoles, 68%) and decomposed at 236° C., but darkened above 200° C. It could be recrystallized to fine crystals by dissolving in hot cyclohexanone (1 g/10 ml) and adding an equal volume of ethanol.

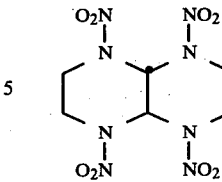

1,4,5,8-Tetranitro-1,4,5,8-tetraazadecalin (TNAD)

TNAD has rather interesting physical properties. It is more heat stable than RDX (1,3,5-trinitro-1,3,5-hexahydrotriazine) and is less sensitive to impact than both RDX or HMX (1,3,5,7-tetranitro-1,3,5,7-tetraazacyclooctane). It has essentially the same density as RDX and only a slightly lower calculated detonation velocity. TNAD is used both as a propellant and an explosive.

| Physical Properties of TNAD | |
| --- | --- |
| Density (g/cm$^3$) | 1.80 |
| Detonation Velocity (mm/$\mu$s) calculated | 8.21 |
| Impact Sensitivity (2.5 kg wt) | 40 cm |
| Melting Point | 232–234° C. |

While the invention has been described in connection with specific embodiments thereof, it will be understood that it is capable of further modification, and this application is intended to cover any variation, uses or adaptation of the invention. It will, therefore, be recognized that the invention is not to be considered as limited to the precise embodiments shown and described but is to be interpreted as broadly as permitted by the appended claims.

What is claimed is:

1. Trans-1,4,5,8-tetranitro-1,4,5,8-tetraazadecalin.

* * * * *